(12) United States Patent
Lim et al.

(10) Patent No.: US 7,432,398 B2
(45) Date of Patent: Oct. 7, 2008

(54) INORGANIC ACID SALTS OF SIBUTRAMINE

(75) Inventors: Dong Kwon Lim, Gyeonggi-do (KR); Eun Young Yang, Gyeonggi-do (KR); Jae Kyoung Ko, Incheon (KR); Kwang Do Choi, Gyeonggi-do (KR); Yong Sik Youn, Gyeonggi-do (KR); Hea Ran Suh, Gyeonggi-do (KR); Chang Ju Kim, Gyeonggi-do (KR)

(73) Assignee: CJ Corporation, Seoul (KR)

( * ) Notice: Subject to any disclaimer, the term of this patent is extended or adjusted under 35 U.S.C. 154(b) by 0 days.

(21) Appl. No.: 10/580,136

(22) PCT Filed: Jan. 6, 2006

(86) PCT No.: PCT/KR2006/000073

§ 371 (c)(1),
(2), (4) Date: Mar. 2, 2007

(87) PCT Pub. No.: WO2006/073292

PCT Pub. Date: Jul. 13, 2006

(65) Prior Publication Data

US 2007/0191489 A1    Aug. 16, 2007

(30) Foreign Application Priority Data

Jan. 6, 2005    (KR) ............... 10-2005-0001405

(51) Int. Cl.
C07C 211/63    (2006.01)
A61K 31/14    (2006.01)

(52) U.S. Cl. ............... 564/282; 564/283; 564/289; 514/643

(58) Field of Classification Search ............... None
See application file for complete search history.

(56) References Cited

U.S. PATENT DOCUMENTS

| 6,331,571 B1 | 12/2001 | Jerussi et al. |
|---|---|---|
| 2004/0068018 A1 | 4/2004 | Lee et al. |
| 2007/0191481 A1 | 8/2007 | Lim et al. |
| 2007/0191482 A1 | 8/2007 | Choi et al. |

FOREIGN PATENT DOCUMENTS

| WO | WO 95/21615 A1 | 8/1995 |
|---|---|---|
| WO | WO 98/13034 A1 | 4/1998 |
| WO | WO 00/56310 A1 | 9/2000 |
| WO | WO 00/56313 A1 | 9/2000 |

OTHER PUBLICATIONS

Database CAPLUS on STN, Acc. No. 2004:690754, Athayde, BR 2001005486 (Oct. 7, 2003) (abstract).*
Database CAPLUS on STN, Acc. No. 1987:623314, Jeffery et al., GB 2184122 (Jun. 17, 1987) (abstract).*
International Search Report for International Application No. PCT/KR2006/000073, mailed Apr. 14, 2006, Korean Intellectual Property Office, Republic of Korea.
Office Action for U.S. Appl. No. 10/580,135, Lim et al., 35 U.S.C. § 371 date: Mar. 2, 2007, International Filing Date: Jan. 6, 2006, mailed on Oct. 4, 2007.
Office Action for U.S. Appl. No. 10/580,132, Choi et al., 35 U.S.C. § 371 date: May 2, 2007, International Filing Date: Jan. 6, 2006, mailed on Oct. 4, 2007.
Database CAPLUS, Accession No. 2004:965047, Document No. 141:400964, record and English language abstract for Lulla et al., "Pharmaceutical formulation comprising anti-obesity agent and acidulant," International Patent Application Publication No. WO2004096202. (2004).
Database CAPLUS, Accession No. 2001:526047, Document No. 135:122299, record and English language abstract for Senanayake et al., "Synthesis of racemic and optically pure desmethylsibutramine, didesmethylsibutramine, oral formulations comprised thereof and their use as dopamine reuptake inhibitors," International Patent Application Publication No. WO2001051453. (2001).
Database CAPLUS, Accession No. 2001:565912, Document No. 135:111957, record and English language abstract for Fu et al., "Preparation of monohydrate of N,N-dimethyl-1-(1-(4-chlorophenyl)cyclobutyl)-3-methylbutylamine hydrochloride," Chinese Patent No. 1125032. (2001).
Database CAPLUS, Accession No. 2004:690754, Document No. 141:179571, record for Athayde, A., "Preparation of sibutramine hydrogensulfate," Brazilian Patent Application No. 2001005486. (2004).
Database Delphion, record for Athayde, A., "Process is for obtaining sulphate of 1-(4-chlorophenyl)-N,N-dimethyl-alpha-(2-methylpropyl)-cyclobutanomethamine and its isomers," Brazilian Patent Application No. 2001000005486. (2003).

* cited by examiner

*Primary Examiner*—Brian J Davis
(74) *Attorney, Agent, or Firm*—Sterne, Kessler, Goldstein & Fox PLLC (57) ABSTRACT

Disclosed are novel inorganic acid salts of sibutramine, which have good physicochemical properties, and crystalline forms thereof. Also disclosed are pharmaceutical compositions comprising the compounds as effective ingredients, methods of preparing the compounds, and the use of the compounds.

13 Claims, 10 Drawing Sheets

INORGANIC ACID SALTS OF SIBUTRAMINE

TECHNICAL FIELD

The present invention relates to novel inorganic acid salts of sibutramine (N,N-dimethyl-1-[1-(4-chlorophenyl)cyclobutyl]-3-methylbutylamine), represented by Chemical Formula 1, below, and crystalline forms thereof. The present invention is also concerned with pharmaceutical compositions comprising the compounds as effective ingredients, methods of preparing the compounds, and the use of the compounds.

[Chemical Formula 1]

X = HSO$_4$, Br, H$_2$PO$_4$·H$_2$O

BACKGROUND ART

Sibutramine (N-[1-[1-(4-chlorophenyl)cyclobutyl]-3-methylbutyl]-N,N-dimethylamine), which is a inhibitor of 5-hydroxytryptamine and noradrenaline reuptake in vivo (Neuropharmacology, 28, p129-134), is useful in the treatment of depression, Parkinson's disease, obesity, insulin-independent diabetes mellitus, epilepsy, and the like. In addition, sibutramine reduces body weight gain by a dual action to reduce food intake by enhancing satiety and to increase energy expenditure by stimulating heat generation (Int. J. Obesity, 19, p145; Brit. J. Pharmacol. 114, p388).

Since sibutramine is difficult to purify due to its low melting point, it is preferable to use a crystalline material capable of being purified by recrystallization in order to prepare a pharmaceutical composition comprising sibutramine. Korean Pat. Publication No. 1990-0000274 discloses that sibutramine is utilized as salts formed with acids providing non-toxic acid addition salts containing pharmaceutically acceptable anions, for example, in the form of hydrochloride, malate, acetate, citrate, fumarate, tartrate, succinate, aspartate or glutmate salt. However, since sibutramine hydrochloride is difficult to handle pharmaceutically due to its hygroscopic nature, it is undesirable to use sibutramine hydrochloride for preparing medicaments. In the preparation of medicaments, a constant weight of an active compound should be contained in each dosage form, but an active ingredient absorbing water from the surrounding environment makes it difficult to achieve such consistency. Korean Pat. Publication No. 94-8913 discloses that when sibutramine hydrochloride is prepared in a monohydrate form, a non-hygroscopic product is obtained, which is suitable for the preparation of capsules, tablets and other pharmaceutical dosage forms.

The therapeutic use of sibutramine in depression is described in British Pat. No. 2098602. The therapeutic use of sibutramine in Parkinson's disease is disclosed in International Pat. Publication No. WO88/06444. The therapeutic use of sibutramine in cerebral function disorders is disclosed in U.S. Pat. No. 4,939,175. The use of sibutramine hydrochloride in the treatment of obesity is disclosed in European Pat. No. 397831. Also, International Pat. Publication No. WO95/20949 discloses the use of sibutramine for improving impaired glucose tolerance or glucose tolerance in patients suffering from insulin-independent diabetes mellitus.

In addition, Brazilian Pat. Publication No. 0105486 discloses a novel salt of sibutramine, sibutramine sulfate, in which two moles of sibutramine are bonded to one mole of sulfuric acid. However, this compound is structurally different from sibutramine hydrogen sulfate (in which one mole of sibutramine is bonded to one mole of sulfuric acid) according to the present invention. In particular, the Brazilian Patent Publication never mentions crystalline forms or physical properties, such as solubility and stability, of the novel salt.

Typically, the preparation of salts having pharmaceutically useful physical properties must satisfy the following physicochemical criteria: (1) good solubility, (2) good stability, (3) good non-hygroscopicity and (4) compressibility into tablet form.

However, Korean Pat. Publication No. 94-8913 states that sibutramine hydrochloride has been known to contain a variable amount of water and thus be hygroscopic, and that non-hygroscopic sibutramine can be obtained by preparing sibutramine hydrochloride in a monohydrate form. Sibutramine hydrochloride monohydrate has been prepared by bringing it into contact with a medium consisting of water or a medium containing water.

Thus, sibutramine hydrochloride monohydrate is prepared by a complicated process including adding a predetermined amount of water to a reaction mixture, or including preparing sibutramine hydrochloride anhydrate and suspending the sibutramine hydrochloride anhydrate in a water-containing solvent for a long time with agitation. In addition, since currently available sibutramine hydrochloride monohydrate has relatively low solubility between pH 1.0 and pH 7.4, substitute salts having better solubility need to be developed in order to improve the bioavailability of sibutramine. The term "sibutramine", as used herein, refers to racemic sibutramine, unless otherwise indicated.

Based on this background, the present inventors found that hydrogen sulfate and bromate salts of sibutramine possess remarkably high solubility in water as well as having non-hygroscopicity and stability, and that sibutramine phosphate hydrate has greatly enhanced solubility even when it exists in a hydrous form, compared to conventional sibutramine hydrochloride hydrate, thereby leading to the present invention.

DISCLOSURE OF THE INVENTION

In this regard, intensive and through research into the development of a novel salt of sibutramine, capable of solving the problems encountered in the prior art, conducted by the present inventors, resulted in the finding that inorganic acid salts of sibutramine, particularly hydrogen sulfate, bromate, and phosphate monohydrate, possess good physicochemical properties (solubility, non-hygroscopicity and stability). The present inventors further found that sibutramine anhydrate can be prepared with no additional complicated procedure of adding a predetermined amount of water in order to prepare a hydrous form of sibutramine, and has remarkably high solubility although it is in an anhydrous form, as well as being non-hygroscopic, and that the inorganic acids used are less-toxic acids that have been used in many medicaments, thereby leading to the present invention.

It is therefore an object of the present invention to provide a pharmaceutical composition for treating and preventing pathological states of obesity and related disorders, comprising an inorganic acid salt of sibutramine, which has increased water solubility, is non-hygroscopic, and is stable to heat, as an active ingredient.

It is another object of the present invention to provide the inorganic acid salt of sibutramine, and a method of preparing the same.

It is a further object of the present invention to provide anhydrous crystalline and hydrous crystalline forms of the inorganic acid salt of sibutramine.

It is yet another object of the present invention to provide a pharmaceutical composition comprising the inorganic acid salt of sibutramine as an effective ingredient along with a pharmaceutically acceptable diluent or carrier.

It is still another object of the present invention to provide a method of treating obesity, depression, Parkinson's disease, insulin-independent diabetes mellitus and epilepsy using the inorganic acid salt of sibutramine as an effective ingredient.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

To accomplish the objects of the present invention, the present invention provides inorganic acid salts of sibutramine, preferably crystalline sibutramine hydrogen sulfate and crystalline sibutramine bromate in anhydrous forms, and crystalline sibutramine phosphate monohydrate in a hydrous form.

The present invention also provides a method of preparing an inorganic acid salt of sibutramine, comprising reacting sibutramine with an inorganic acid selected from among sulfuric acid, bromic acid, and phosphoric acid in an inert solvent.

The present invention further provides methods of preparing anhydrous crystalline and hydrous crystalline forms of an inorganic acid salt of sibutramine.

The present invention still further provides a pharmaceutical composition for treating obesity, comprising a therapeutically effective amount of an inorganic acid salt of sibutramine and a pharmaceutically acceptable diluent or carrier. The present invention provides a method of treating obesity, comprising administering the therapeutically effective amount of the inorganic acid salt of sibutramine.

The present invention still further provides a pharmaceutical composition for treating depression, comprising a therapeutically effective amount of an inorganic acid salt of sibutramine and a pharmaceutically acceptable diluent or carrier. The present invention provides a method of treating depression, comprising administering the therapeutically effective amount of the inorganic acid salt of sibutramine.

The present invention still further provides a pharmaceutical composition for treating Parkinson's disease, comprising a therapeutically effective amount of an inorganic acid salt of sibutramine and a pharmaceutically acceptable diluent or carrier. The present invention provides a method of treating Parkinson's disease, comprising administering the therapeutically effective amount of the inorganic acid salt of sibutramine.

The present invention still further provides a pharmaceutical composition for treating insulin-independent diabetes mellitus, comprising a therapeutically effective amount of an inorganic acid salt of sibutramine and a pharmaceutically acceptable diluent or carrier. The present invention provides a method of treating insulin-independent diabetes mellitus, comprising administering the therapeutically effective amount of the inorganic acid salt of sibutramine.

The present invention still further provides a pharmaceutical composition for treating epilepsy, comprising a therapeutically effective amount of an inorganic acid salt of sibutramine and a pharmaceutically acceptable diluent or carrier. The present invention provides a method of treating epilepsy, comprising administering the therapeutically effective amount of the inorganic acid salt of sibutramine.

The pharmaceutical composition of the present invention is preferably formulated into tablets or capsules.

Hereinafter, the present invention will be described in more detail.

The present invention relates to an inorganic acid salt of sibutramine, represented by Chemical Formula 1.

[Chemical Formula 2]

Sibutramine bromate anhydrate according to the present invention displays solubility, non-hygroscopicity, formulability and chemical stability, identical to or better than the commercially available sibutramine hydrochloride monohydrate of Chemical Formula 2. Sibutramine hydrogen sulfate and sibutramine phosphate hydrate exhibit non-hygroscopicity, formulability chemical stability and flowability, identical to or better than sibutramine hydrochloride monohydrate, and in particular exhibit about at least 10 times greater solubility in distilled water and buffer solutions of pH 1.2, pH 4.0, pH 5.3, pH 6.8 and pH 7.4. With respect to non-hygroscopicity, the aforementioned inorganic acid salts of sibutramine display no hygroscopicity and no decrease in water content when they are exposed to relative humidities of 10%, 75% and 90% for a period of seven days or longer. With respect to stability, the inorganic acid salts of sibutramine do not generate impurities and do not change in content even when they are exposed to a high temperature of 60° C. for a period of one month or longer. The inorganic acid salts of sibutramine also exhibit good photostability.

The present inventors learned about that the sulfuric, phosphoric and bromic acids, contained in the inorganic acid salts of sibutramine according to the present invention, are typically used in a number of medicaments and are less-toxic acids that have been proven safe for long-term use, and concluded that the novel inorganic acid salts of sibutramine are suitable for long-term administration, thereby leading to the present invention.

The inorganic acid salts of sibutramine according to the present invention may be crystalline or non-crystalline. Crystalline forms of the inorganic acid salts of sibutramine are preferred with respect to physical properties such as non-hygroscopicity and thermodynamical stability.

The present invention includes a method of preparing the inorganic acid salt of sibutramine. That is, the present invention includes a method of preparing an inorganic acid salt of sibutramine, comprising reacting sibutramine with an inorganic acid in an inert solvent. The reaction using sulfuric acid among inorganic acids used takes place according to the following Reaction 1.

[Reaction 1]

Among the inorganic acids used as reactants, sulfuric acid has a reported oral-rat $LD_{50}$ of 2,140 mg/kg, and has been used in a number of medicaments, including clopidogrel, cefpirome, amphetamine, salbutamol and gentamycin.

In an embodiment, a first crystalline sibutramine hydrogen sulfate is prepared using acetone, ethyl acetate, ethanol, acetonitrile, methylethyl ketone or methylene chloride as an inert solvent according to the method. This compound is characterized by having an X-ray diffraction pattern in which peaks ($I/I_0 \geqq 200$) appear at 2θ values of 6.50, 12.18, 12.38, 12.58, 13.06, 14.00, 16.76, 17.04, 18.06, 19.68, 20.32, 20.63, 21.34, 21.82, 22.28, 22.54, 23.32, 24.50, 25.80, 26.42, 28.24, 28.64, 29.28, and 33.34.

Figure 1:
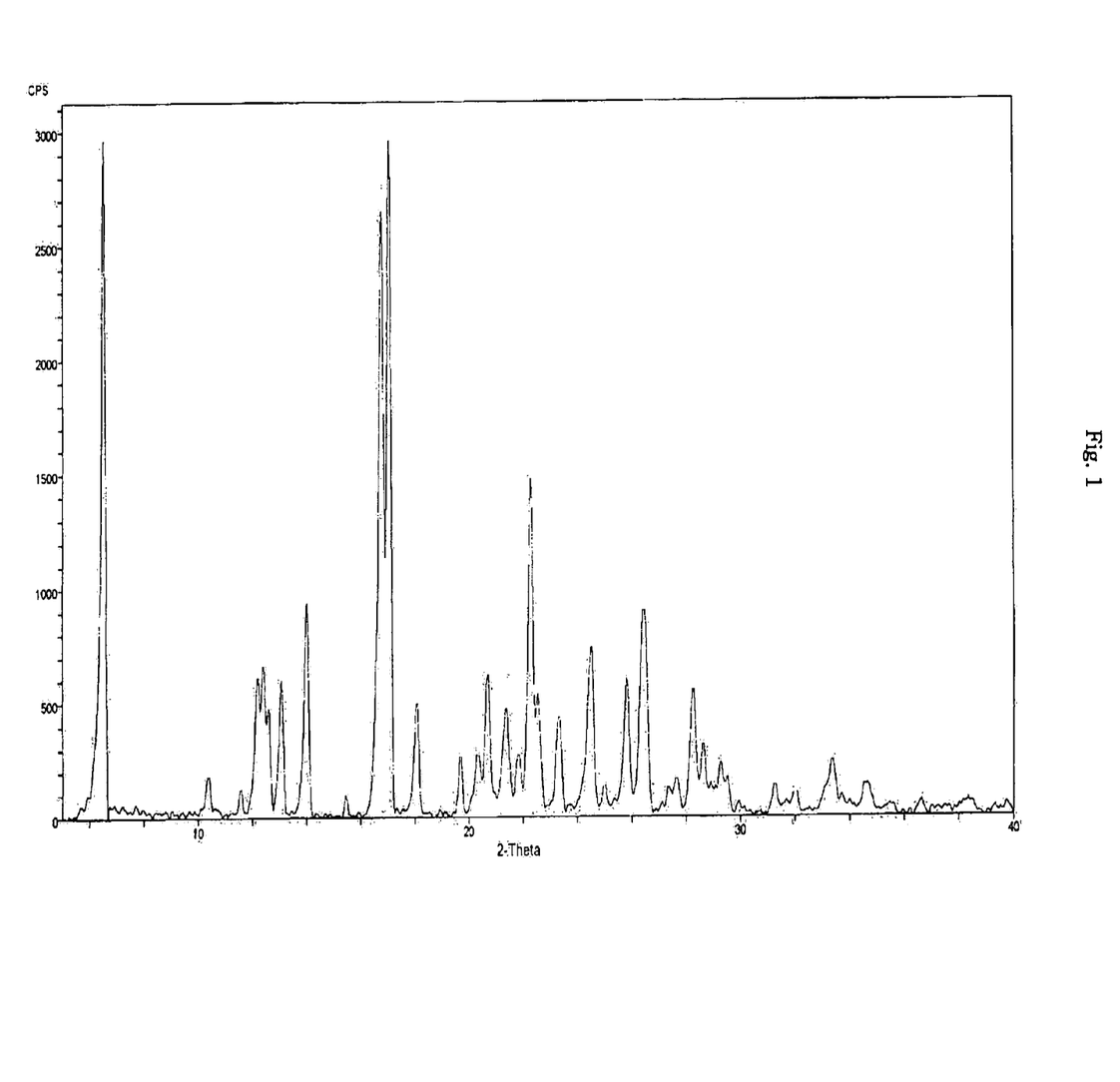
FIG. 1 is an X-ray diffraction spectrum of a first crystalline sibutramine hydrogen sulfate according to Example 1.
Figure 2:
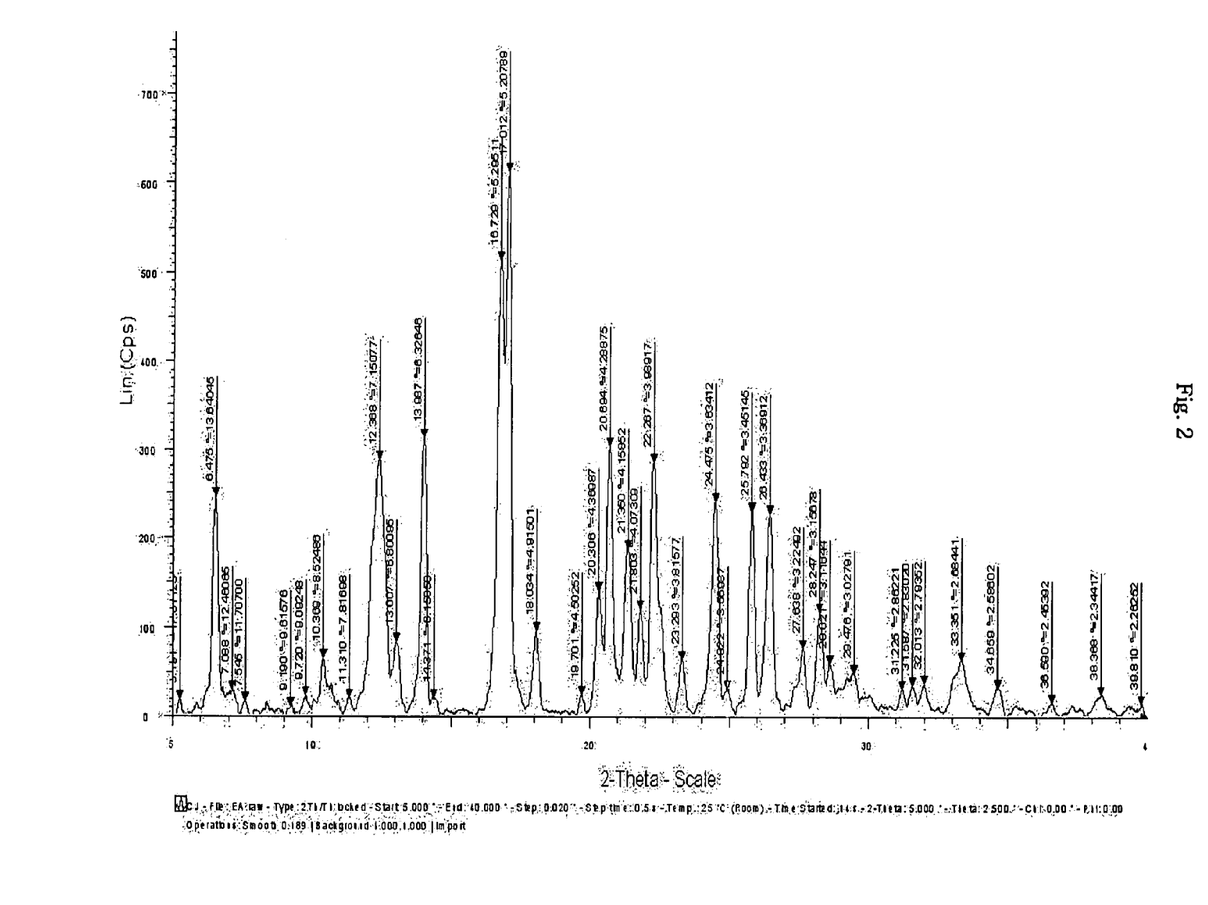
FIG. 2 is an X-ray diffraction spectrum of a first crystalline sibutramine hydrogen sulfate according to Example 2.
Figure 3:
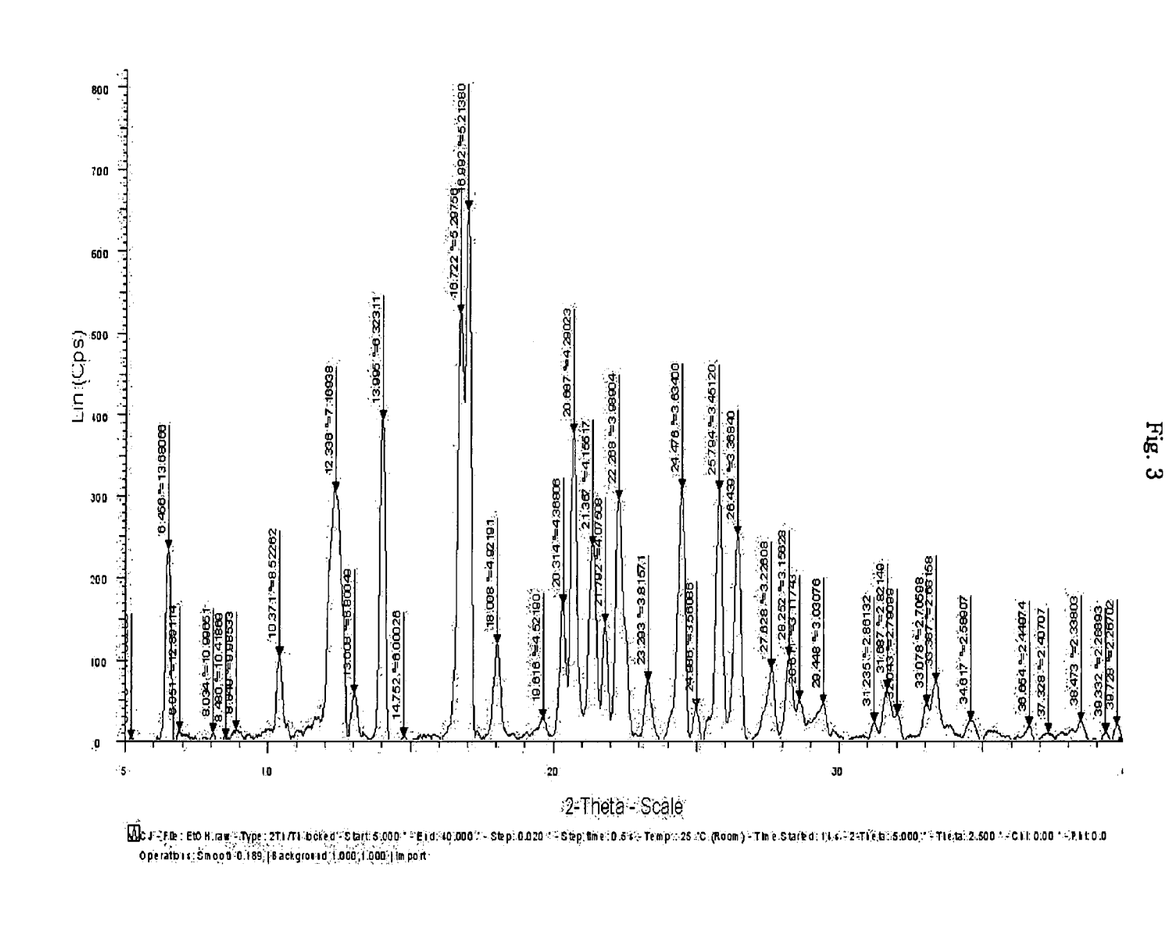
FIG. 3 is an X-ray diffraction spectrum of a first crystalline sibutramine hydrogen sulfate according to Example 3.
Figure 4:
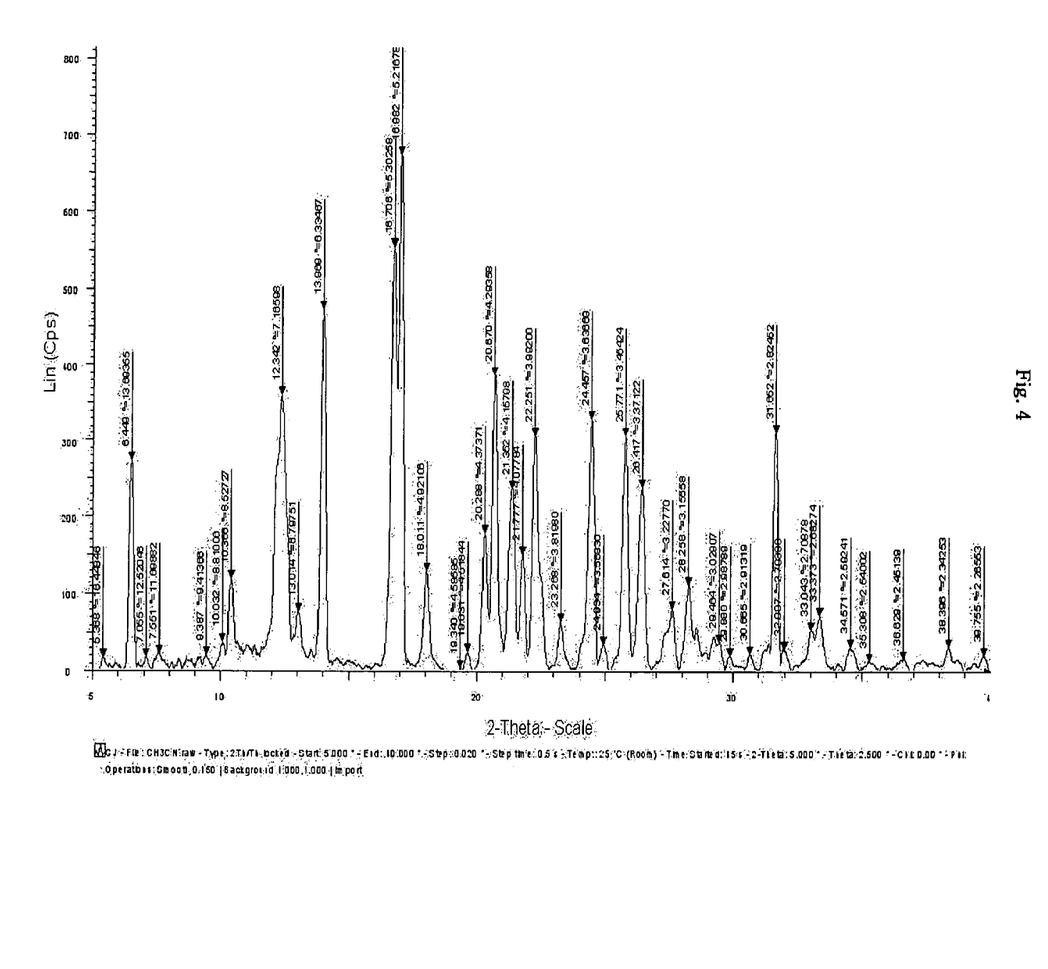
FIG. 4 is an X-ray diffraction spectrum of a first crystalline sibutramine hydrogen sulfate according to Example 4.
Figure 5:
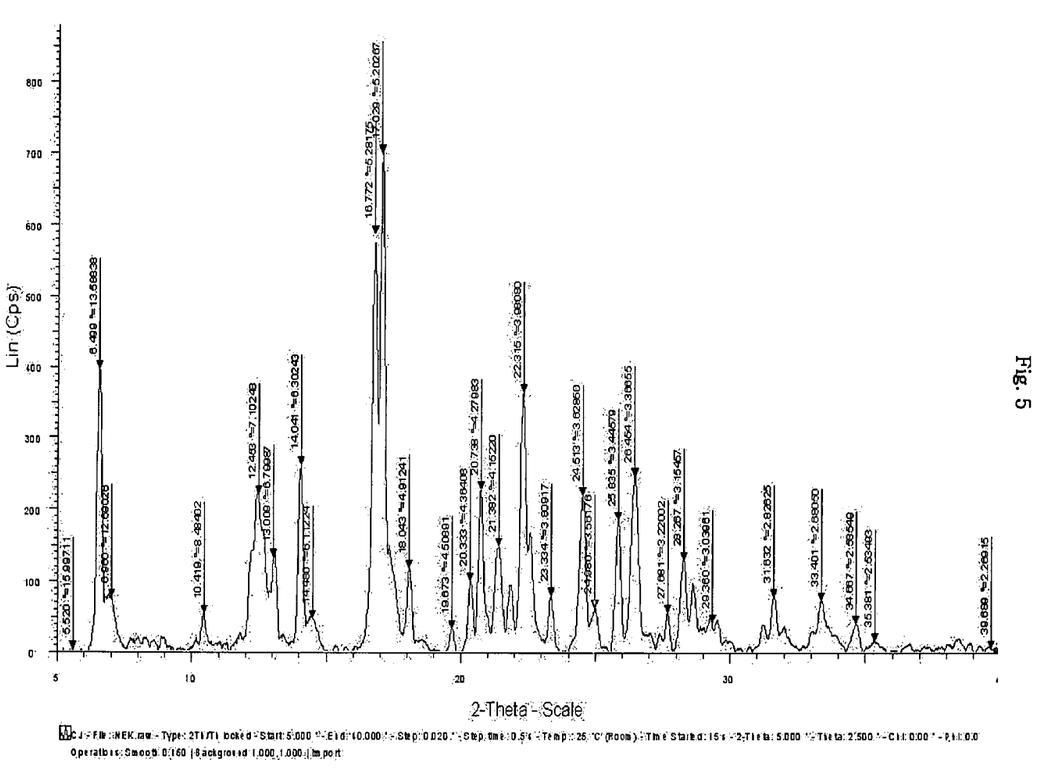
FIG. 5 is an X-ray diffraction spectrum of a first crystalline sibutramine hydrogen sulfate according to Example 5.
Figure 6:
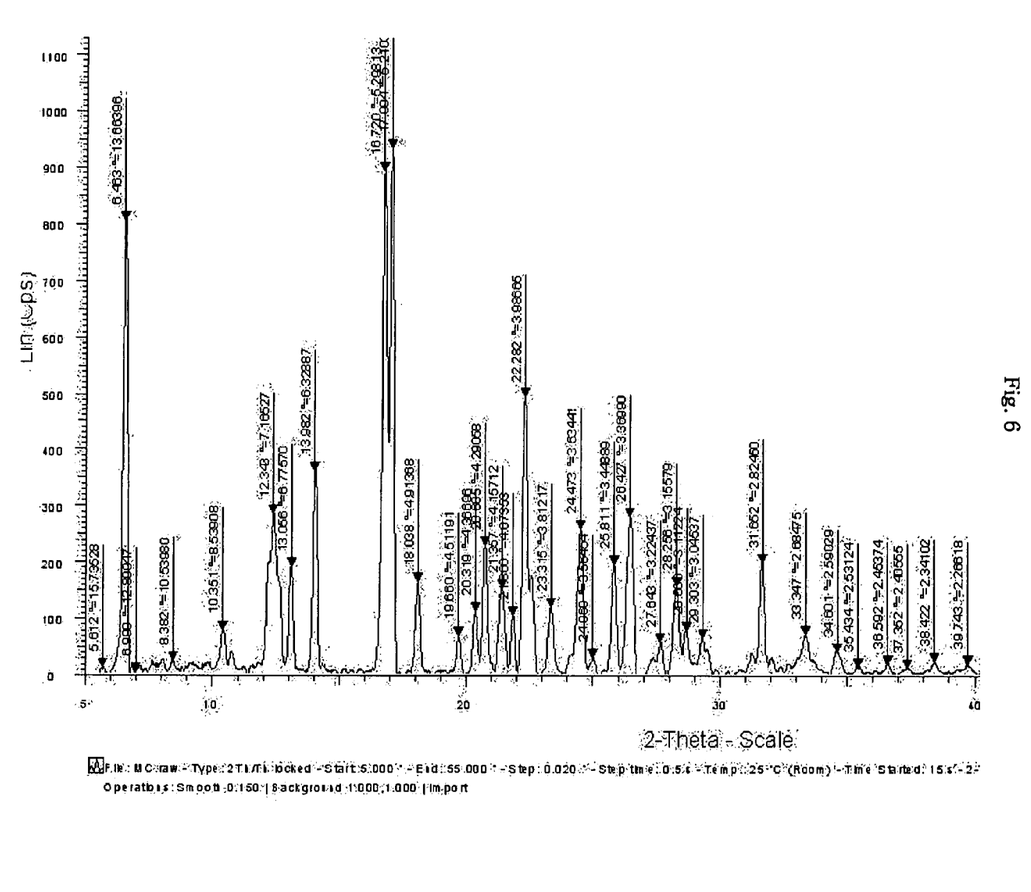
FIG. 6 is an X-ray diffraction spectrum of a first crystalline sibutramine hydrogen sulfate according to Example 6.
Figure 7:
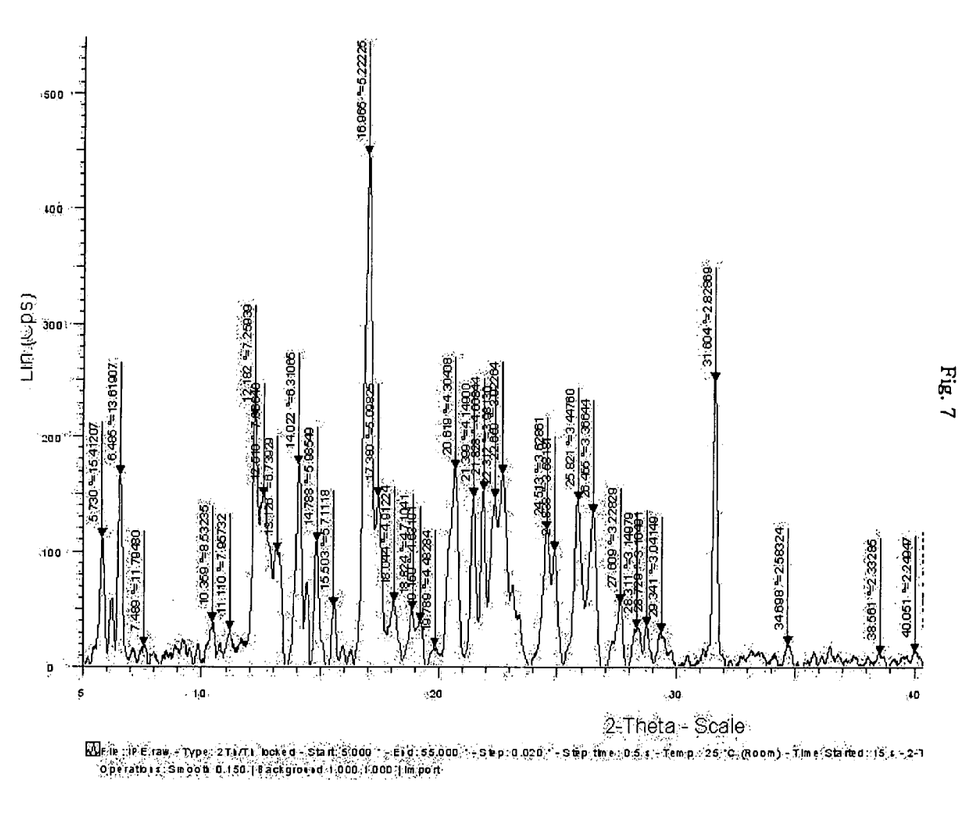
FIG. 7 is an X-ray diffraction spectrum of a second crystalline sibutramine hydrogen sulfate according to Example 7.

In another embodiment, a second crystalline sibutramine hydrogen sulfate is prepared using isopropylether as an inert solvent according to the method. This compound is characterized by having an X-ray diffraction pattern in which peaks ($I/I_0 \geqq 100$) appear at 2θ values of 5.73, 6.49, 12.18, 12.51, 13.13, 14.02, 14.79, 16.97, 17.38, 20.62, 21.40, 21.83, 22.31, 22.68, 24.51, 24.88, 25.82, 26.45, and 31.60.

Figure 8:
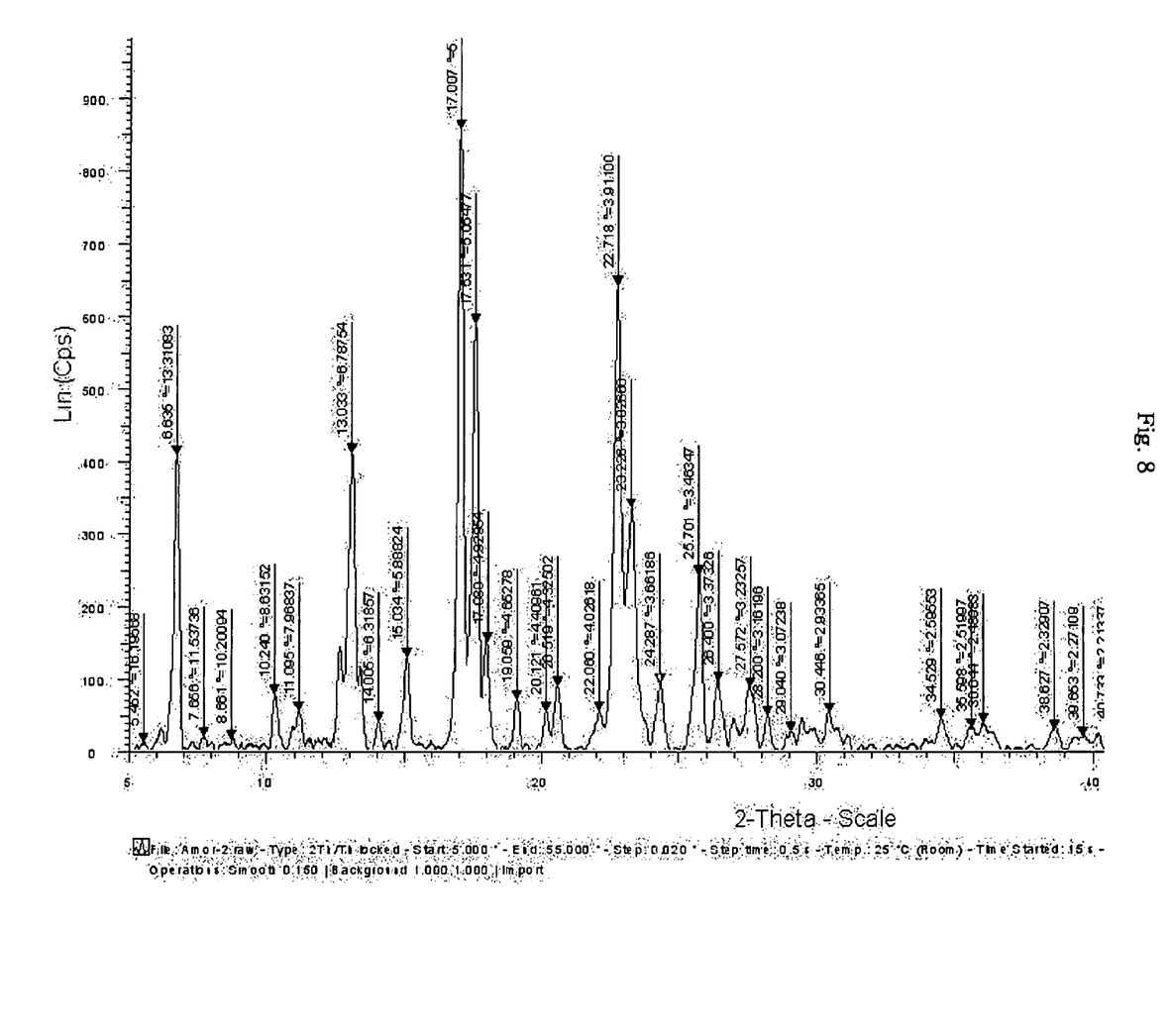
FIG. 8 is an X-ray diffraction spectrum of a third crystalline sibutramine hydrogen sulfate according to Example 8.

In a further embodiment, a third crystalline sibutramine hydrogen sulfate is prepared using methanol and isopropylether as an inert solvent mixture according to the method. This compound is characterized by having an X-ray diffraction pattern in which peaks ($I/I_0 \geqq 100$) appear at 2θ values of 6.64, 10.24, 13.03, 15.04, 17.00, 17.53, 17.08, 19.06, 20.52, 22.72, 23.23, 24.23, 25.70, 26.40, and 27.57.

The reaction using bromic acid among inorganic acids used takes place according to the following Reaction 2.

[Reaction 2]

Figure 9:
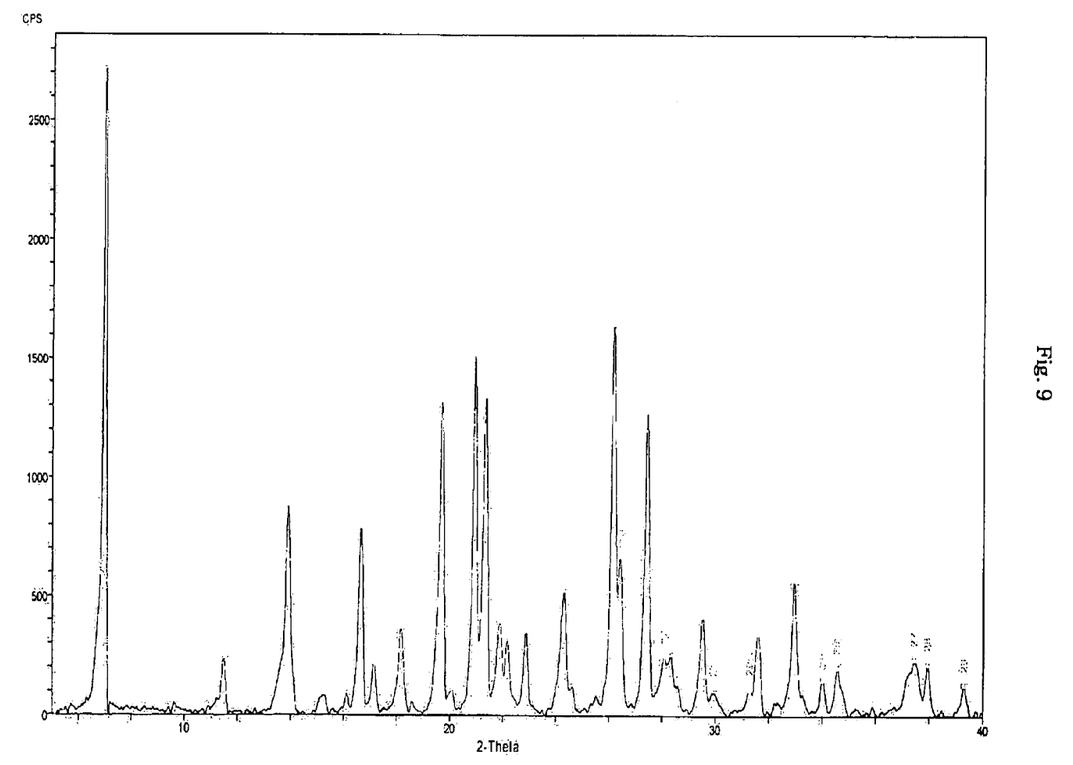
FIG. 9 is an X-ray diffraction spectrum of crystalline sibutramine bromate according to Example 9.

The bromic acid used as a reactant has a reported oral-mouse $LD_{50}$ of 2,700 mg/kg, and has been used in a number of medicaments, including citalopram, dextromethorphan, fenoterol, galantamine and scopolamine. In detail, the product of Reaction 2, crystalline sibutramine bromate, is characterized by having an X-ray diffraction pattern in which peaks ($I/I_0 \geqq 200$) appear at 2θ values of 6.96, 11.48, 13.88, 16.64, 17.14, 18.14, 19.68, 20.92, 21.32, 21.86, 22.16, 22.86, 24.30, 26.16, 26.40, 27.42, 28.06, 28.32, 29.52, 31.58, 32.94, 34.54, 37.42, and 37.82.

The reaction using phosphoric acid among inorganic acids used takes place according to the following Reaction 3.

[Reaction 3]

Figure 10:
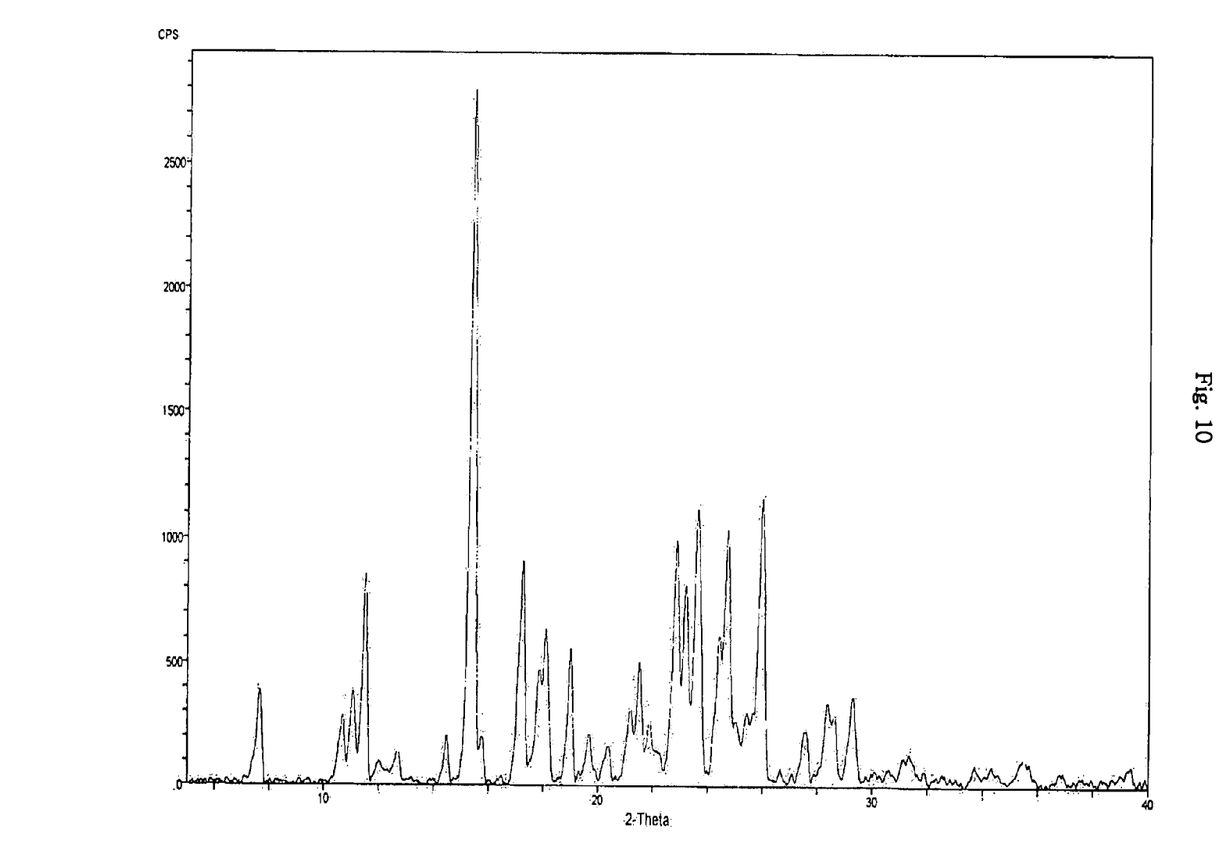
FIG. 10 is an X-ray diffraction spectrum of crystalline sibutramine phosphate hydrate according to Example 10.

The phosphoric acid used as a reactant has a reported oral-rat $LD_{50}$ of 1,530 mg/kg, and has been used in a number of medicaments, including clindamycin, chloroquine, codeine, disopyramide, metromidazole and oleandomycin. In detail, the product of Reaction 3, crystalline sibutramine phosphate, is characterized by having an X-ray diffraction pattern in which peaks ($I/I_0 \geqq 200$) appear at 2θ values of 7.66, 10.68, 11.06, 11.50, 14.46, 15.40, 15.74, 17.22, 17.84, 18.08, 18.98, 19.68, 21.18, 21.50, 21.88, 22.84, 23.18, 23.62, 24.42, 24.72, 25.98, 27.52, 28.38, 28.64, and 29.28.

The inorganic acids used in Reactions 1, 2 and 3 are are less-toxic acids that haven't been proven safe for long-term use.

The inert solvent available in the preparation method of the present invention includes acetone, ethyl acetate, methanol, ethanol, isopropanol, acetonitrile, isopropyl ether, methylethyl ketone and dichloromethane. Acetone and ethyl acetate are preferred.

In the inert solvent, one equivalent of sibutramine may be reacted with 1 to 2 equivalents, preferably 1.02 to 1.2 equivalents, of concentrated sulfuric acid, at −5 to 40° C., preferably 20 to 30° C., for 0.5 to 5 hours, preferably 2 to 3 hours. Herein, the concentrated sulfuric acid is used after being diluted with the inert solvent.

The preparation method of the present invention may provide an inorganic acid salt of sibutramine in a yield of higher than 90.0% and a high purity of greater than 99.0%.

The present invention provides a pharmaceutical composition for treating or preventing pathological states of obesity and related disorders, comprising a therapeutically effective amount of hydrogen sulfate, bromate or phosphate monohydrate of sibutramine and a pharmaceutically acceptable diluent or carrier, and a method of treating or preventing pathological states of obesity and related disorders by administering this composition.

The present invention also provides a pharmaceutical composition for treating depression, comprising a therapeutically effective amount of an inorganic acid salt of sibutramine and a pharmaceutically acceptable diluent or carrier, and a method of treating depression by administering this composition.

The present invention further provides a pharmaceutical composition for treating or preventing Parkinson's disease, comprising a therapeutically effective amount of an inorganic acid salt of sibutramine and a pharmaceutically acceptable diluent or carrier, and a method of treating or preventing Parkinson's disease by administering this composition.

The present invention still further provides a pharmaceutical composition for treating insulin-independent diabetes mellitus, comprising a therapeutically effective amount of an inorganic acid salt of sibutramine and a pharmaceutically acceptable diluent or carrier, and a method of treating insulin-independent diabetes mellitus by administering this composition.

The present invention still further provides a pharmaceutical composition for treating epilepsy, comprising a therapeutically effective amount of an inorganic acid salt of sibutramine and a pharmaceutically acceptable diluent or carrier, and a method of treating epilepsy by administering this composition.

The pharmaceutical composition comprising the inorganic acid salt of sibutramine according to the present invention as an active ingredient may be preferably administered orally, for example in the form of tablets or capsules.

Tablets may be prepared by mixing an active ingredient with a carrier, a diluent or an excipient and compressing the mixture into tablets. Examples of suitable carriers, diluents or excipients include disintegrators such as starch, sugars and mannitol; fillers and extenders such as calcium phosphate and silicic derivatives; binding agents such as carboxymethyl cellulose and other cellulose derivatives, gelatin and polyvinyl pyrrolidone; and lubricants such as talc, calcium and magnesium stearate, and solid polyethylene glycol. Also, hard or soft gelatin capsules containing an active ingredient, either with or without an additive such as the carriers, diluents or excipients may be prepared according to an ordinary method.

The pharmaceutical composition preferably contains a crystalline inorganic acid salt of sibutramine, represented by Chemical Formula 1, as an active ingredient in an amount of 1 to 50 parts by weight based on 250 parts by weight of the composition.

For example, the pharmaceutical composition having a total weight of 250 mg according to the present invention may be prepared in such a manner as to contain 10 mg (based on sibutramine content) of the crystalline inorganic acid salt of sibutramine, represented by Chemical Formula 1, 115 mg of microcrystalline cellulose, 115 mg of lactose, 5 mg of silicon dioxide, and 5 mg of magnesium stearate. However, this composition of the pharmaceutical composition is illustrative, and thus, the scope of the present invention is not limited thereto.

A better understanding of the present invention may be obtained through the following examples which are set forth to illustrate, but are not to be construed as the limit of the present invention.

Reference Example 1

Preparation of Sibutramine Hydrochloride Monohydrate

Sibutramine hydrochloride anhydrate was prepared according to a method described in Korean Pat. No. 2098602 or Korean Pat. Publication No. 90-00274. Then, according to a method described in British Pat. No. 2184122 or Korean Pat. Publication No. 94-08913, 10 g of the prepared sibutramine hydrochloride anhydrate was dissolved in a boiling mixture of 110 ml acetone and 1.2 ml water, and the resulting solution was hot-filtered and distilled to remove 80 ml of the solvent, thus reducing the volume of the filtrate. The concentrate was filtered to recover a generated solid. The solid was vacuum-dried, thus obtaining 9.2 g (yield: 87%) of the compound of Chemical Formula 2, which had a melting point of 195° C.

EXAMPLES

Hydrogen sulfate, bromate and phosphate monohydrate salts of sibutramine were prepared according to the preparation method of the present invention, and were compared with sibutramine hydrochloride hydrate for physical properties including hygroscopicity, solubility, stability, light stability and crystallizability. In addition, the inorganic acid salts of sibutramine were formulated into capsules in order to examine their formulability and release patterns.

Example 1

Preparation of Sibutramine Hydrogen Sulfate Using Acetone

Sibutramine (17.1 g, 0.06 mol) was dissolved in 150 ml of acetone with agitation. After the solution was adjusted to 25° C., 6.0 g of concentrated sulfuric acid was diluted with 50 ml of acetone and added to the solution. Crystals formed slowly. The resulting mixture was agitated at 25° C. for 2 hrs and further agitated at 4° C. for 1 hr. The generated solid was recovered by filtration under pressure, washed with 30 ml of acetone, and vacuum-dried at 40° C., thus obtaining 21.0 g (yield: 91%) of a target compound.

TABLE 1

| Elemental analysis ($C_{17}H_{28}ClNO_4S$) | Unit (%) |
|---|---|
| Measured value | C: 54.35, H: 7.68, N: 3.82, O: 17.00, S: 8.58 |
| Theoretical value | C: 54.03, H: 7.47, N: 3.71, O: 16.93, S: 8.4 |

Melting point (DSC): 212.8° C.

$^1$H-NMR (δ, DMSO-d6): 8.39 (1H, br, s), 7.54~7.49 (4H, dd), 3.75 (1H, t), 2.83 (3H, d), 2.5 (2H, d), 2.33 (2H, t), 2.13 (3H, d), 1.90 (1H, m), 1.70~1.67 (2H, m), 1.40 (2H, m), 1.00 (6H, t)

Example 2

Preparation of Sibutramine Hydrogen Sulfate Using Ethyl Acetate

Sibutramine (17.1 g, 0.06 mol) was dissolved in 150 ml of ethyl acetate with agitation. After the solution was adjusted to 25° C., 6.0 g of concentrated sulfuric acid was diluted with 50 ml of ethyl acetone and added to the solution. Crystals formed slowly. The resulting mixture was agitated at 25° C. for 2 hrs and further agitated at 4° C. for 1 hr. The generated solid was recovered by filtration under pressure, washed with 50 ml of ethyl acetate, and vacuum-dried at 40° C., thus obtaining 21.5 g (yield: 94%) of a target compound.

Melting point: 212° C.

Example 3

Preparation of Sibutramine Hydrogen Chloride Using Ethanol

Sibutramine (17.1 g, 0.06 mol) was dissolved in 70 ml of ethanol with agitation. After the solution was adjusted to 25° C., 6.0 g of concentrated sulfuric acid was diluted with 10 ml of ethanol and added to the solution to slowly form crystals. The resulting mixture was agitated at 25° C. for 2 hrs and further agitated at 4° C. for 1 hr. The generated solid was recovered by filtration under pressure, washed with 50 ml of acetone, and vacuum-dried at 40° C., thus obtaining 20.3 g (yield: 89.5%) of a target compound.

Melting point: 211° C.

Example 4

Preparation of Sibutramine Hydrogen Chloride Using Acetonitrile

Sibutramine (17.1 g, 0.06 mol) was dissolved in 150 ml of acetonitrile with agitation. After the solution was adjusted to 25° C., 6.0 g of concentrated sulfuric acid was diluted with 50 ml of acetonitrile and added to the solution. Crystals formed slowly. The resulting mixture was agitated at 25° C. for 2 hrs and further agitated at 4° C. for 1 hr. The generated solid was recovered by filtration under pressure, washed with 50 ml of acetonitrile, and vacuum-dried at 40° C., thus obtaining 21.0 g (yield: 92%) of a target compound.

Melting point: 211° C.

Example 5

Preparation of Sibutramine Hydrogen Sulfate Using Methylethyl Ketone

Sibutramine (17.1 g, 0.06 mol) was dissolved in 150 ml of methylethyl ketone with agitation. After the solution was adjusted to 25° C., 6.0 g of concentrated sulfuric acid was diluted with 50 ml of methylethyl ketone and added to the solution. Crystals formed slowly. The resulting mixture was agitated at 25° C. for 2 hrs and further agitated at 4° C. for 1 hr. The generated solid was recovered by filtration under pressure, washed with 50 ml of methylethyl ketone, and vacuum-dried at 40° C., thus obtaining 22.0 g (yield: 97%) of a target compound.

Melting point: 212° C.

Example 6

Preparation of Sibutramine Hydrogen Sulfate Using Methylene Chloride

Sibutramine (17.1 g, 0.06 mol) was dissolved in 150 ml of methylene chloride with agitation. After the solution was adjusted to 25° C., 6.0 g of concentrated sulfuric acid was diluted with 50 ml of methylene chloride and added to the solution. Crystals formed slowly. The resulting mixture was agitated at 25° C. for 2 hrs and further agitated at 4° C. for 1 hr. The generated solid was recovered by filtration under pressure, washed with 50 ml of methylene chloride, and vacuum-dried at 40° C., thus obtaining 20.3 g (yield: 90%) of a target compound.

Melting point: 211° C.

Example 7

Preparation of Sibutramine Hydrogen Sulfate Using Isopropyl Ether

Sibutramine (17.1 g, 0.06 mol) was dissolved in 150 ml of isopropyl ether with agitation. After the solution was adjusted to 25° C., 6.0 g of concentrated sulfuric acid was diluted with 50 ml of isopropyl ether and added to the solution. Crystals formed immediately after isopropyl ether addition. The resulting mixture was agitated at 25° C. for 2 hrs and further agitated at 4° C. for 1 hr. The generated solid was recovered by filtration under pressure, washed with 50 ml of isopropyl ether, and vacuum-dried at 40° C., thus obtaining 22.1 g (yield: 97%) of a target compound.

Melting point: 207° C.

Example 8

Preparation of Sibutramine Hydrogen Sulfate Using Methanol and Isopropyl Ether Sibutramine (17.1 g, 0.06 mol) was dissolved in 50 ml of methanol with agitation. After the solution was adjusted to 25° C., 6.0 g of concentrated sulfuric acid was diluted with 10 ml of methanol and added to the solution. The reaction solution was concentrated from 30 ml to 15 ml under pressure. 150 ml of isopropyl ether was slowly added in droplets to the concentrate for 10 min. The resulting mixture was agitated at 25° C. for 2 hrs and further agitated at 4° C. for 1 hr. The generated solid was recovered by filtration under pressure, washed with 50 ml of isopropyl ether, and vacuum-dried at 40° C., thus obtaining 20.3 g (yield: 90%) of a target compound.

Melting point: 210° C.

Example 9

Preparation of Sibutramine Bromate

Sibutramine (28.0 g, 0.1 mol) was dissolved in 280 ml of ethyl acetate with agitation. After the solution was adjusted to 25° C., 17.2 g of 47% bromic acid was slowly added in droplets to the solution to form crystals. The resulting mixture was agitated at 25° C. for 2 hrs and further agitated at 4° C. for 1 hr. The generated solid was recovered by filtration under pressure, washed with 100 ml of ethyl acetate, and vacuum-dried at 40° C., thus obtaining 33.1 g (yield: 92%) of a target compound.

TABLE 2

| Elemental analysis ($C_{17}H_{27}BrClN$) | Unit (%) |
|---|---|
| Measured value | C: 56.79, H: 7.77, N: 3.89 |
| Theoretical value | C: 56.60, H: 7.54, N: 3.88 |

Melting point (DSC): 212.4° C.

$^1$H-NMR (δ, DMSO-d6): 8.61 (1H, br, s), 7.60~7.48 (4H, dd), 3.80 (1H, t), 2.83 (3H, d), 2.50 (2H, d), 2.32 (2H, t), 2.20 (3H, d), 1.90 (1H, m), 1.77~1.68 (2H, m), 1.39 (2H, m), 1.00 (6H, t)

Example 10

Preparation of Sibutramine Phosphate Monohydrate 10 g of sibutramine was dissolved in 100 ml of ethyl acetate with agitation. After the solution was adjusted to 25° C., 4.13 g of 85% phosphoric acid was diluted with 30 ml of ethyl acetate and added in droplets to the solution. Crystals formed slowly. The resulting mixture was agitated at 25° C. for 2 hrs. The generated solid was recovered by filtration under pressure and washed with 30 ml of ethyl acetate. The washed sibutramine phosphate anhydrate was mixed with 120 ml of isopropyl ether, 50 ml of acetone and 1.5 ml of water, agitated at 20-30° C. for 18 hrs, filtered, and vacuum-dried, thus obtaining 12.8 g (yield: 90%) of a target compound.

The obtained sibutramine phosphate monohydrate was subjected to elemental analysis and melting point analysis, and the results are as follows.

TABLE 3

| Elemental analysis ($C_{17}H_{31}ClNO_5P$) | Unit (%) |
|---|---|
| Measured value | C: 51.38, H: 7.69, N: 3.50, O: 19.62 |
| Theoretical value | C: 51.58, H: 7.89, N: 3.54, O: 20.21 |

Melting point (DSC): 174.1° C.

$^1$H-NMR (δ, DMSO-d6): 8.14 (1H, br, s), 7.38~7.30 (4H, dd), 3.14 (1H, t), 2.51 (1H, d), 2.45 (1H, d), 2.33 (1H, m), 2.22 (5H, t), 2.18 (3H, t), 1.90 (1H, m), 1.67 (1H, m), 1.56 (1H, m), 1.19 (2H, m), 0.95 (3H, d), 0.89 (3H, d)

Example 11

Preparation of Capsules Containing Sibutramine Hydrogen Sulfate

Ingredients were mixed according to the composition described in Table 4, below, to prepare capsules containing sibutramine hydrogen sulfate.

TABLE 4

| Ingredients | Content (per capsule) |
|---|---|
| Sibutramine hydrogen sulfate | Amount corresponding to 10 mg of sibutramine |
| Lactose | 115 mg |
| Microcrystalline cellulose | 115 mg |
| Silicon dioxide | 5 mg |
| Magnesium stearate | 5 mg |

The ingredients were mixed and filled into hard capsules using a capsule filling machine (Bosche).

Example 12

Preparation of Capsules Containing Sibutramine Bromate

Ingredients were mixed according to the composition described in Table 5, below, to prepare capsules containing sibutramine bromate.

TABLE 5

| Ingredients | Content (per capsule) |
|---|---|
| Sibutramine bromate | Amount corresponding to 10 mg of sibutramine |
| Lactose | 115 mg |
| Microcrystalline cellulose | 115 mg |
| Silicon dioxide | 5 mg |
| Magnesium stearate | 5 mg |

The ingredients were mixed and filled into hard capsules using a capsule filling machine (Bosche).

Example 13

Preparation of Capsules Containing Sibutramine Phosphate Monohydrate

Ingredients were mixed according to the composition described in Table 6, below, to prepare capsules containing sibutramine phosphate monohydrate.

TABLE 6

| Ingredients | Content (per capsule) |
|---|---|
| Sibutramine phosphate monohydrate | Amount corresponding to 10 mg of sibutramine |
| Lactose | 115 mg |
| Microcrystalline cellulose | 115 mg |
| Silicon dioxide | 5 mg |
| Magnesium stearate | 5 mg |

The ingredients were mixed and filled into hard capsules using a capsule filling machine (Bosche).

Example 14

Evaluation of Hygroscopicity of the Inorganic Acid Salts of Sibutramine

The inorganic acid salts of sibutramine, prepared in Examples 1, 2 and 3, and sibutramine hydrochloride monohydrate were exposed to humid conditions (75% and 90% RH) at 25□ for a period of three days or one weeks. Then, the water content (K.F. water %) of the samples was measured. The results are given in Table 7, below.

TABLE 7

| | Storage humidity (relative humidity) | | | | |
|---|---|---|---|---|---|
| | 75% | | | 90% | |
| | Storage period | | | | |
| | Initial | 3 days | | 1 week | |
| Sibutramine hydrogen sulfate | 0.02% | 0.02% | 0.01% | 0.03% | 0.03% |
| sibutramine bromate | 0.09% | 0.09% | 0.09% | 0.08% | 0.08% |
| Sibutramine phosphate hydrate | 4.25% | 4.24% | 4.25% | 4.25% | 4.26% |
| Sibutramine HCl hydrate | 5.5% | 5.49% | 5.5% | 5.5% | 5.49% |

As shown in Table 7, like sibutramine hydrochloride hydrate, hydrogen sulfate, bromate and phosphate hydrate salts of sibutramine displayed almost no change in water content under humid conditions.

Example 15

Evaluation of Solubility of the Inorganic Acid Salts of Sibutramine

The inorganic acid salts of sibutramine, prepared in Examples 1, 2 and 3, and sibutramine hydrochloride monohydrate were evaluated for solubility in solutions having various pH values. The results are given in Table 8, below. In Table 8, the solubility is expressed as milligrams (mg) of sibutramine dissolved per milliliter (ml) of solution.

TABLE 8

| | Salts of sibutramine | | | | |
|---|---|---|---|---|---|
| Solvents | Hydrogen sulfate | Bromate | Phosphate | Hydrochloride | Remarks |
| DW | 285 | 12.78 | 38.86 | 26.18 | Dissolved at 37° C. |
| pH 1.2 | 333 | 12.43 | 23.92 | 13.36 | |
| pH 4.0 | 333 | 3.64 | 50 | 9.58 | |
| pH 5.3 | 400 | 8.96 | 50 | 6.58 | |
| pH 6.8 | 370 | 11.08 | 24.55 | 23.14 | |
| pH 7.4 | 400 | 12.41 | 50 | 9.2 | |

As shown in Table 8, in distilled water (DW) and buffer solutions at various pH values, hydrogen sulfate and phosphate salts of sibutramine had greatly enhanced solubility compared to sibutramine hydrochloride. These results indicate that these salt forms of sibutramine may have better bioavailability than sibutramine hydrochloride monohydrate.

Example 16

Evaluation of Stability of the Inorganic Acid Salts of Sibutramine

The inorganic acid salts of sibutramine, prepared in Examples 1, 2 and 3, and sibutramine hydrochloride monohydrate were exposed to a stringent 60° C. heat treatment. The results are summarized in Table 9, below.

TABLE 9

| | Storage period | | | |
|---|---|---|---|---|
| | Initial | 1 wk | 2 wks | 4 wks |
| Hydrogen sulfate | 1.000 | 1.000 | 0.999 | 0.999 |
| Bromate | 1.000 | 0.999 | 1.000 | 0.999 |
| Phosphate | 1.000 | 1.000 | 0.999 | 1.000 |
| Hydrochloride | 1.000 | 1.000 | 0.999 | 0.999 |

HPLC was performed under the following conditions.
Wavelength of UV detection: 225 nm
Column: octadecyl silica gel, C18 (4.6×150 mm, 5 μm)
Mobile phase: ammonium phosphate monohydride (0.05 M, adjusted to pH 6.0 with phosphoric acid):acetonitrile=35:65
Flow rate: 1.0 ml/min As shown in Table 9, like sibutramine hydrochloride monohydrate, the inorganic acid salts of sibutramine displayed almost no change in content upon stringent 60° C. heat treatment. These results indicate that the hydrogen sulfate, bromate and phosphate monohydrate salts of sibutramine, like sibutramine hydrochloride monohydrate, have good chemical stability at high temperature.

Example 17

Valuation of Light Stability of the Inorganic Acid Salts of Sibutramine

A light stability test was performed as follows. The inorganic acid salts of sibutramine, prepared in Examples 1, 2 and 3, and sibutramine hydrochloride monohydrate were exposed to fluorescent light at 25° C. using a light stability test chamber suitable for the ICH guideline, for storage periods of 1, 2 and 4 weeks. The results are given in Table 10, below.

TABLE 10

| | Storage period | | | |
|---|---|---|---|---|
| | Initial | 1 wk | 2 wks | 4 wks |
| Hydrogen sulfate | 1.000 | 1.000 | 1.000 | 0.999 |
| Bromate | 1.000 | 1.000 | 0.999 | 0.999 |
| Phosphate monohydrate | 1.000 | 1.000 | 0.999 | 0.999 |
| HCl monohydrate | 1.000 | 1.000 | 0.999 | 0.999 |

As shown in Table 10, when content changes of the inorganic acid salts of sibutramine were analyzed by HPLC in order to determine their light stability, the inorganic acid salts of sibutramine, like sibutramine hydrochloride monohydrate, displayed good light stability.

INDUSTRIAL APPLICABILITY

The hydrogen sulfate, bromate and phosphate monohydrate salts of sibutramine according to the present invention have good physicochemical properties including non-hygroscopicity, solubility, stability, formulability and crystallizability. The hydrogen sulfate and phosphate monohydrate salts of sibutramine exhibit an increased solubility, more than 10 times that of sibutramine hydrochloride hydrate. In addition, due to their non-hygroscopic nature, since the hydrogen sulfate, bromate and phosphate monohydrate salts of sibutramine do not change in content, they are highly suitable for long-term storage and guarantee consistency suitable for the preparation of pharmaceutical dosage forms.

Moreover, since sulfuric, bromic and phosphoric acids used in the preparation of the novel inorganic acid salts of sibutramine are less-toxic acids that haven't been proven to be pharmaceutically safe for long-term use, the inorganic acid salts of sibutramine are useful as novel salts of sibutramine.

The invention claimed is:

1. An inorganic acid salt of sibutramine, which has a structure of the following Chemical Formula 1:

[Chemical Formula 1]

X = HSO$_4$, Br, H$_2$PO$_4$·H$_2$O the inorganic acid salt being hydrogen sulfate, bromate, or phosphate monohydrate.

2. The inorganic acid salt of sibutramine as set forth in claim 1, wherein the sibutramine hydrogen sulfate is a first crystalline sibutramine hydrogen sulfate having an X-ray diffraction pattern in which peaks appear at 2θ values of 6.50, 12.18, 12.38, 12.58, 13.06, 14.00, 16.76, 17.04, 18.06, 19.68, 20.32, 20.63, 21.34, 21.82, 22.28, 22.54, 23.32, 24.50, 25.80, 26.42, 28.24, 28.64, 29.28, and 33.34.

3. The inorganic acid salt of sibutramine as set forth in claim 1, wherein the sibutramine hydrogen sulfate is a second crystalline sibutramine hydrogen sulfate having an X-ray diffraction pattern in which peaks appear at 2θ values of 5.73, 6.49, 12.18, 12.51, 13.13, 14.02, 14.79, 16.97, 17.38, 20.62, 21.40, 21.83, 22.31, 22.68, 24.51, 24.88, 25.82, 26.45, and 31.60.

4. The inorganic acid salt of sibutramine as set forth in claim 1, wherein the sibutramine hydrogen sulfate is a third crystalline sibutramine hydrogen sulfate having an X-ray diffraction pattern in which peaks appear at 2θ values of 6.64, 10.24, 13.03, 15.04, 17.00, 17.53, 17.08, 19.06, 20.52, 22.72, 23.23, 24.23, 25.70, 26.40, and 27.57.

5. The inorganic acid salt of sibutramine as set forth in claim 1, wherein the sibutramine bromate is crystalline sibutramine bromate having an X-ray diffraction pattern in which peaks appear at 2θ values of 6.96, 11.48, 13.88, 16.64, 17.14, 18.14, 19.68, 20.92, 21.32, 21.86, 22.16, 22.86, 24.30, 26.16, 26.40, 27.42, 28.06, 28.32, 29.52, 31.58, 32.94, 34.54, 37.42, and 37.82.

6. The inorganic acid salt of sibutramine as set forth in claim 1, wherein the sibutramine phosphate monohydrate is crystalline sibutramine phosphate monohydrate having an X-ray diffraction pattern in which peaks appear at 2θ values of 7.66, 10.68, 11.06, 11.50, 14.46, 15.40, 15.74, 17.22, 17.84, 18.08, 18.98, 19.68, 21.18, 21.50, 21.88, 22.84, 23.18, 23.62, 24.42, 24.72, 25.98, 27.52, 28.38, 28.64, and 29.28.

7. A method of preparing sibutramine bromate comprising reacting sibutramine and bromic acid.

8. A method of preparing sibutramine phosphate or phosphate monohydrate comprising reacting sibutramine and phosphoric acid.

9. The method as set forth in claim 7 or 8, wherein the reaction takes place in an organic solvent selected from the group consisting of acetone, ethyl acetate, methanol, ethanol, isopropanol, acetonitrile, isopropyl ether, methylethyl ketone, dichloromethane and combinations thereof.

10. A pharmaceutical composition comprising an inorganic acid salt of sibutramine represented by the following Chemical Formula 1:

[Chemical Formula 1]

$X = HSO_4, Br, H_2PO_4 \cdot H_2O$ and a pharmaceutically acceptable diluent or carrier.

11. The pharmaceutical composition as set forth in claim 10, wherein the sibutramine hydrogen sulfate, sibutramine bromate or sibutramine phosphate is contained in a therapeutically effective amount of 1 to 50 mg.

12. A method of treating obesity, depression, Parkinson's disease, insulin-independent diabetes mellitus or epilepsy, comprising administering a—pharmaceutical composition comprising an inorganic acid salt of sibutramine represented by the following Chemical Formula 1:

[Chemical Formula 1]

$X = HSO_4, Br, H_2PO_4 \cdot H_2O$ and a pharmaceutically acceptable diluent or carrier.

13. The pharmaceutical composition as set forth in claim 10, wherein the composition is for treating obesity, depression, Parkinson's disease, insulin-independent diabetes mellitus, or epilepsy.

* * * * *